(12) United States Patent
Seyr et al.

(10) Patent No.: US 11,602,444 B2
(45) Date of Patent: Mar. 14, 2023

(54) JOINT DEVICE, HYDRAULIC UNIT AND METHOD FOR CONTROLLING A JOINT DEVICE

(71) Applicant: Otto Bock Healthcare Products GmbH, Vienna (AT)

(72) Inventors: Martin Seyr, Vienna (AT); Harald Sima, Herzogenburg (AT); Roland Auberger, Vienna (AT)

(73) Assignee: OTTO BOCK HEALTHCARE PRODUCTS GMBH, Wein (AT)

( * ) Notice: Subject to any disclaimer, the term of this patent is extended or adjusted under 35 U.S.C. 154(b) by 192 days.

(21) Appl. No.: 16/339,682

(22) PCT Filed: Oct. 6, 2017

(86) PCT No.: PCT/EP2017/075573
§ 371 (c)(1),
(2) Date: May 16, 2019

(87) PCT Pub. No.: WO2018/065615
PCT Pub. Date: Apr. 12, 2018

(65) Prior Publication Data
US 2019/0307582 A1  Oct. 10, 2019

(30) Foreign Application Priority Data
Oct. 6, 2016 (DE) .................... 102016118999.5

(51) Int. Cl.
*A61F 2/64* (2006.01)
*A61F 2/74* (2006.01)
(Continued)

(52) U.S. Cl.
CPC .................. *A61F 2/70* (2013.01); *A61F 2/64* (2013.01); *A61H 1/0274* (2013.01); *A61H 3/00* (2013.01);
(Continued)

(58) Field of Classification Search
CPC ................ A61F 2/64; A61F 2002/5006; A61F 2002/503; A61F 2002/5038;
(Continued)

(56) References Cited

U.S. PATENT DOCUMENTS 2,480,856 A    9/1949  Henschke
3,236,157 A *  2/1966  Lovell .................. F03C 1/0076
                                                             91/49
(Continued)

FOREIGN PATENT DOCUMENTS

CN   105769395 A    7/2016
DE       8122676 U1   11/1981
(Continued)

OTHER PUBLICATIONS

International Search Report for International Application No. PCT/EP2017/075573 dated Jan. 23, 2018, 3 pages.

*Primary Examiner* — Bruce E Snow
(74) *Attorney, Agent, or Firm* — Holland & Hart LLP

(57) ABSTRACT

A joint device with an upper part and a lower part which are mounted on each other so as to be pivotable about a pivot axis, a hydraulic unit secured on the upper part and the lower part, and a housing in which a cylinder is arranged. A working piston is arranged in the cylinder and is coupled to at least one spring mechanism which transmits tensile forces and compressive forces and which engages on at least one abutment arranged displaceably inside the cylinder.

20 Claims, 15 Drawing Sheets

(51) Int. Cl.
   *A61F 2/70* (2006.01)
   *A61H 3/00* (2006.01)
   *B25J 9/00* (2006.01)
   *A61H 1/02* (2006.01)
   *A61F 5/01* (2006.01)
   *A61F 2/50* (2006.01)
   *A61F 2/60* (2006.01)
   *A61F 2/76* (2006.01)

(52) U.S. Cl.
   CPC .............. *B25J 9/0006* (2013.01); *A61F 2/60* (2013.01); *A61F 2/74* (2021.08); *A61F 2/748* (2021.08); *A61F 2002/503* (2013.01); *A61F 2002/5006* (2013.01); *A61F 2002/5038* (2013.01); *A61F 2002/5073* (2013.01); *A61F 2002/7635* (2013.01); *A61F 2002/7645* (2013.01); *A61F 2005/0155* (2013.01); *A61F 2005/0169* (2013.01)

(58) Field of Classification Search
   CPC .......... A61F 2002/745; A61F 2002/748; A61F 2002/7635; A61F 2002/7645; A61F 2/74
   See application file for complete search history.

(56) References Cited

U.S. PATENT DOCUMENTS

| | | | |
|---|---|---|---|
| 3,605,960 A | 9/1971 | Singer | |
| 5,376,138 A * | 12/1994 | Bouchard | A61F 2/64 188/315 |
| 5,728,174 A * | 3/1998 | Fitzlaff | A61F 2/68 623/46 |
| 5,948,021 A * | 9/1999 | Radcliffe | A61F 2/68 623/44 |
| 6,106,560 A | 8/2000 | Boender | |
| 6,997,959 B2 | 2/2006 | Chen et al. | |
| 8,928,161 B2 | 1/2015 | Loverich | |
| 8,974,543 B2 | 3/2015 | Balboni | |
| 2014/0128993 A1 | 5/2014 | Shen | |
| 2015/0164660 A1 | 6/2015 | Will | |
| 2015/0182354 A1 | 7/2015 | Bonnet | |
| 2015/0202057 A1 * | 7/2015 | Zahedi | A61F 2/6607 623/26 |

FOREIGN PATENT DOCUMENTS

| | | |
|---|---|---|
| DE | 9405545 U1 | 8/1994 |
| DE | 20306821 U1 | 6/2003 |
| DE | 102008045113 A1 | 3/2010 |
| DE | 102012013141 | 5/2014 |
| DE | 102012013141 A1 | 5/2014 |
| FR | 24035 E | 2/1922 |
| FR | 530887 | 3/1922 |
| SU | 1577785 | 7/1990 |
| WO | 1992022267 A1 | 12/1992 |
| WO | 2012151515 A | 8/2012 |

* cited by examiner

JOINT DEVICE, HYDRAULIC UNIT AND METHOD FOR CONTROLLING A JOINT DEVICE

TECHNICAL FIELD

The invention relates to a joint device with an upper part and a lower part, which are mounted on each other so as to be pivotable about a pivot axis, with a hydraulic unit secured to the upper part and the lower part, with a housing in which a cylinder is arranged, in which a working piston connected to a piston rod is mounted displaceably and divides the cylinder into two chambers. The invention likewise relates to such a hydraulic unit and a method for setting and operating such a joint device, which can in particular be used in orthotic or prosthetic devices. Orthotic or prosthetic devices should be understood in particular as ortheses, prostheses, and exoskeletons. The hydraulic unit can also be used in robotics.

BACKGROUND

In orthotic or prosthetic devices, frequently two components are mounted relative to one another, for example an upper part and a lower part are pivoted about a joint axis relative to one another in an orthotic joint or a prosthetic joint; likewise there can be longitudinally sliding relative movements between orthotic or prosthetic components. Frequently it is necessary to damp the relative movement. To this end hydraulic and/or pneumatic dampers are used which damp an extension or flexion of the rotating joint or a sliding movement in one direction or another. The dampers call be made to be adjustable so as to provide altered resistances against the relative movement over the course of a movement on the basis of sensor data or established control curves. For this purpose, valves or throttles which may be adjustable are provided in the flow channels.

So as to support movement of the components of the orthotic or prosthetic device, actuators are provided which for example can be configured as electric motors. Likewise hydraulic or pneumatic drives can be provided. By means of energy storage devices, it is possible to store kinetic energy so that in the further course of the movement cycle or at some other point in time, this stored energy which was acquired for example from braking of a flexion movement can be returned to the system. The orthotic or prosthetic device is driven by the energy return, so that an actuator is provided. The energy of a movement is supportively supplied via an actuator.

DE 10 2012 013 141 A1 discloses an orthotic or prosthetic joint device with an upper part and a lower part pivotably arranged thereon with at least one hydraulic unit between the upper part and the lower part, which has a piston movably mounted in a housing with an extension chamber and a flexion chamber, which is coupled to the upper part or the lower part. By means of a pressure supplying device, the piston can be acted upon with a pressure wherein the pressure supplying device has at least one pressure storage, which may be optionally coupled via a switching device to an extension chamber or a flexion chamber. The pressure storage can be coupled to a pump so as to fill the pressure storage via the pump. The disadvantage of such a design is the comparatively great space requirement due to the external pressure storage.

For prosthetic feet or ortheses with a foot part in which a hydraulic unit is used, in order to damp a joint device or to control the behavior of the joint device, there is the problem that a complex adaptation has to be made to different heel heights. Displacement of the zero point of a spring device is complicated. Furthermore, oscillating processes about a starting position without adjustment processes are not provided for. Dissipative processes cannot be easily combined with energy-storing processes.

SUMMARY

It is therefore the object of the present invention to provide a joint device, a hydraulic unit and a method for setting and operating a joint device with which various movements and damping properties can be achieved with the lowest possible adjustment efforts.

According to the invention this object is achieved by means of a joint device as well as with a hydraulic, unit and a method with the features disclosed herein.

The joint device according to the invention with an upper part and a lower part which are mounted on each other so as to be pivotable about a pivot axis, with a hydraulic unit secured on the upper part and the lower part, with a housing in which a cylinder is arranged, in which a working piston connected to a piston rod is mounted displaceably and divides the cylinder into two chambers provides that the working piston is coupled to at least one spring device which transmits tensile and compressive forces and engages on at least one abutment, which is arranged inside the cylinder. Coupling of the spring device to the working piston call be directly mechanical or hydraulic. A hydraulic coupling is present when the spring device acts on the working piston via a hydraulic medium, for example hydraulic oil or water. For this purpose the spring device is coupled with a further hydraulic element, for example a piston. Due to the displaceable arrangement of the abutment or abutments and of the working piston within a chamber, it becomes possible to alter the position of the abutment or abutments and thereby to pre-tension the associated spring device or upon release of the spring device to transmit forces to the working piston. Likewise in this way the position of the working piston within the chamber can be displaced. In particular it is possible with an adjustable zero crossover about which the joint device pivots, to maintain a desired or preset spring action without further adjustment of the abutments or the spring device. After setting a zero crossover, usually no effort or only a slight effort is needed in order to control the further action of the joint device. By means of the bilaterally acting spring device, which acts both in the tensile force and in the compressive force direction, it is possible to pivot the joint device about a zero position or the zero crossover in which the tensile forces and compressive forces are in equilibrium so that in both directions of pivoting about the zero crossover, an energy storage capability of the spring device is provided.

A further development of the invention provides that the abutment is mounted in the chamber as a displaceably mounted separator element or piston, so that the separator element or the piston separates a subchamber from the chamber. The two chambers divided by the working piston in the cylinder, which can also be termed the extension chamber and flexion chamber, are also divided by the separating element or a further piston, which acts as an abutment for the spring device, into two subchambers, of which one is termed the chamber and the other the subchamber. The chamber facing the working piston is termed the chamber and the chamber configured on the side of the separating element facing away from the piston is termed the subchamber. By means of such an embodiment, it is possible to slightly block, switch off or even alter the spring action, by blocking or throttling a hydraulic connection from the subchamber to the chamber or to another chamber or subchamber. Such a blockage or alteration of the spring properties or of the damping properties can be effected especially easily via an adjustment valve, which is arranged on a channel or in a connecting line between the chamber and subchamber or between subchambers.

The chambers and subchambers are preferably hydraulically coupled to one another via channels in which adjustable valves are arranged. Via these valves it is possible to block the movement of the working pistons or to allow movements of the working piston yielding under a load, without significantly altering the spring characteristic. Furthermore, the zero position of the respective spring device, i.e., the position in which tensile forces and compressive forces are in equilibrium, can be adjustable. When all chambers and subchambers are hydraulically connected to one another and via valves the respective access can be throttled or blocked, a plurality of combinations of spring actions or blockages of the joint device is possible without the valves having to be changed over when the direction of movement and/or of forces is changed. The position of the abutments can be set by volume changes, which can be simply implemented and fixed during movement through valve adjustments. Likewise it is possible to implement energy storage in a specific movement phase or displacement position of the joint device, to block a hydraulic volume with a loaded spring device, and to release it at a later time.

The abutment can limit the chambers on the outside, wherein a non-displaceable barrier wall separates the subchambers from the chambers. On the side of the abutment facing away from the working piston or the chamber, no hydraulic fluid need be present, in particular, for a simple design the spring device is arranged outside the chamber. The chambers and subchambers can be connected to one another via adjustable valves arranged in the barrier wall in order to alter the zero position as well as the oscillation behavior or movement behavior of the joint device under stress, or in order to be able to adjust the desired behavior.

The spring device can be configured as a tensile-compressive spring or as a combination of two counteracting tensile and compressive springs or as a combination of two counteracting tensile or compressive springs. The use of a combined tensile-compressive spring has the advantage of a reduction in the partial number, a reduction in the weight, and reduced installation complexity, while the separation of the spring device into tensile spring and compressive spring or counteracting tensile or compressive springs opens up a greater variety of setting possibilities, as the specific springs can be set up for the specific load and adapted to the specific demands.

A further development of the invention provides that the spring device is arranged within a chamber, in particular a subchamber, by which a minimal installation space and integration of all hydraulic components and spring components within the hydraulic unit can be implemented, so that a compact design both of the hydraulic unit and of the joint device is possible. The hydraulic unit then comprises a closed system in which, via valves, the flow resistances of the hydraulic fluid between the chambers and subchambers can be adjusted.

The tensile or compressive spring can be arranged in different subchambers or on a side of the working piston in a chamber and subchamber, so as to be able to provide diverse spring properties and energy storage properties over diverse springs and chambers.

A further development of the invention provides that the spring device holds the upper part in an adjustable starting position relative to the lower part. This is advantageous for example in an embodiment of the joint device as an ankle joint, in order to be able to make an adjustment to different heel heights or an adjustment to deviating ground inclination. In one embodiment of the joint device as an ankle joint, for example in a prosthetic foot or an orthotic foot, the normal gait movement and rolling off movement involves loading of the spring during plantar flexion after heel strike. Then the spring device is unloaded during the dorsal flexion in the first half of the rollover movement. After reaching a starting position the spring unit is loaded again during further rollover with increasing dorsal flexion and then unloads in the unloading phase one last time until toe-off. Here during a plantar flexion the foot is guided to the starting position. The spring device operating in the tensile and compressive direction thus holds the upper part relative to the tower part or the foot relative to the lower leg part in a starting position about which the foot pivots. Pivoting takes place counter to the return force of the spring device both in the plantar flexion direction and in the dorsal flexion direction. By means of the displaceable embodiment of the abutment/abutments and/or of the working piston it is possible to make an adjustment for a different shoe, in particular when there is a change in the heel height, or during execution of the special movement pattern without having to make fluffier changes in control. The spring properties essentially are not altered by the change in the zero crossover or by the change in the starting position. Basically however it is also possible during walking or during movement of the joint device to displace the position of the abutment or abutments so that the spring segment of the spring device can be overlain by a passive yield in the plantar flexion direction and/or dorsal flexion direction. The control effort for displacing the position of the abutment or of some other displacement device for displacing the abutment is comparatively slight and the movement, especially when there is no overlap due to passive yield, is usually elastic, thus energy-saving and energy-releasing during the plantar flexion and dorsal flexion depending on the movement phase, and essentially non-dissipating, which leads to easier walking. Furthermore it is possible, apart from a heel height adjustment and adjustments to the terrain, to block the spring device, for example for standing so that an improved standing stability is provided.

In an embodiment of the joint device as a prosthetic knee joint or orthotic knee joint, the starting position can likewise be freely selected, for example slightly before achieving a maximal extension with a knee joint angle of 180°. The knee joint coming from the swing phase then, before attaining the maximal knee angle, passes through the starting position or the zero crossover, for example in a range of 3° to 8° before reaching a knee angle of 180° so as to compress the spring device in the terminal phase of the swing phase. The spring stiffness as well as the starting position are selected such that based on the mass inertia of the lower leg part and the foot part possibly located thereon a maximal extension is achieved even against the spring device. In the foot placement or at heel strike the knee joint is in an extended position but due to the pre-tensioned spring device in a pre-tensioned position in the direction of a flexion, so that there is support of the standing phase flexion directly after the heel strike due to the releasing spring device. Such behavior is very similar to the physiological gait pattern. Then the spring device during the increasing standing phase flexion is loaded in the flexion direction. After attainment of the maximal standing phase flexion the spring is again unloaded in a standing phase direction so as to reload to the standing phase extension with a maximal extension during the rollover through the starting position. The spring device reloaded in the terminal standing phase will then yield again in the initial swing phase and support the swing phase extension. This behavior can proceed with no or with minimal valve adjustment processes or displacement devices of abutments. During standing, by displacement of the abutment/abutments and/or of the working piston and possibly decoupling of the spring device series, a maximal extension and thereby a stable joint device can be achieved in a simple manner, so that at maximal extension no flexing moments act on the joint device.

In order to identify different movement patterns, a sensor can be arranged in the joint device or allocated to the joint device, for example an inertial angle sensor or several angle sensors which detect the angular positions relative to one another of an upper part or lower part or other ortheses and prostheses components, or other position sensors and/or velocity sensors and/or acceleration sensors, in order to detect the respective gait phases and movement patterns.

The joint device in particular allows oscillation about a preset permanent zero point or about a variable adjustable zero point without a further adjustment of valves during the further movement process. The other spring and damper behaviors are determined by the spring device and the flow conditions within the hydraulic unit. The spring device can be switched off by blocking the hydraulic unit by closing the valves. By displacement of the abutment during walking, dissipative components can be implemented by the hydraulic unit. The joint device can be operated especially simply when there are two abutments in the hydraulic device which are arranged on opposite sides of the working piston so that both in the flexion direction and in the extension direction different positions of the abutment or abutments can be set.

The invention likewise relates to a hydraulic unit as described above, even when it is not built into a joint device.

The method for setting and operating a joint device as described above, with an upper part and a lower part, which are mounted on each other so as to be pivotable about a pivot axis, having a hydraulic unit secured on the upper part and the lower part, with a housing in which a cylinder is arranged, in which a working piston connected to a piston rod is displaceably mounted and divides the cylinder into two chambers, provides that the working piston is coupled to at least one tensile and compressive force transmitting spring device, which engages on at least one abutment preferably displaceably mounted in a chamber, wherein the setting of a zero position of the working piston or a pivoting movement of the upper part relative to a lower part is carried out by opening or adjusting valves in channels. The at least one abutment arranged within the chamber transmits the hydraulic forces to the spring device and back to the working piston and can be adjusted for setting a zero position or during the pivoting movement. By adjusting the zero position of the hydraulic unit it is possible to set a starting position or a zero position in which the respective spring device is not effectively engaged. The joint device can be set such that an adaptation to different design embodiments, for example to different heel heights or to a joint angle to be achieved can be effected. If the abutment or abutments are moved or adjusted during the pivoting movement, a dissipative or energy-storing component is added, wherein the adjustment effort can be kept comparatively low due to the combination of the pivoting movement with a spring device. By means of the spring device, it is possible to provide a free or nearly free force flux during use of the joint device in an orthopedic technical device such as a prosthesis or orthesis, so that a pivoting movement about the starting position or zero position can be achieved without further adjustment of the abutments or by connecting or disconnecting throttles.

The abutment or the position of the abutment is preferably hydraulically adjusted. To this end, it is preferably provided that the abutment is arranged within one of the chambers divided by the working piston and separates a subchamber, which is hydraulically connected to the respective chamber. Via adjustable valves, the position of the abutment can be set and fixed by application of a corresponding force to a joint device. Alternatively, the abutment is adjusted by a motor, for example an electric motor, via a gearing and an adjustment device, for example a screw thread.

The abutment can limit the chamber on the outside, wherein a preferably non-displaceable, at least fixable barrier wall separates the subchambers from the chambers, and the chambers are hydraulically coupled to one another view lines. The respective chamber and the subchambers are connected via adjustable valves, wherein the valves are closed for blocking the joint device. To release the joint device, the necessary valves for that purpose are used.

Preferably the abutment separates a subchamber from the chamber, advantageously an abutment is arranged on both sides of the working piston, thus in both chambers, so that two subchambers are configured, which are arranged on opposite sides of the working piston. The chambers and the subchambers or subchamber, when only one subchamber is present, are hydraulically coupled to one another via lines and valves, wherein the valves are closed for blocking the joint device. For example, during standing it is possible and advantageous if the joint device is blocked, in order to provide maximal safety for the user of the joint device in an orthopedic technical device, such as for example an orthesis or prosthesis. If all valves are closed, the joint device cannot be displaced about the pivot axis. Alternatively it is provided that to release the joint device, the valves allocated to the chambers are opened, which is possible for example during the swing phase when the joint device is used as a knee joint.

For damping the pivoting movement, the valves can be opened only partially, so that a dissipative component can be set based on an increased flow resistance within the channels or connections between the individual chambers or subchambers.

For oscillation about an adjustable zero point, the hydraulic connection between two subchambers lying on opposite sides of the working piston can be closed, and the valves between the chambers on the opposite sides of the working piston at least partially opened, which for example would be an advantageous state of an ankle joint for walking on a flat surface. The connection between the chambers in this case is preferably closed.

A further development of the method provides that the abutment limits the chamber on the outside and a non-displaceable barrier wall separates the subchambers from the chambers, and the chambers are hydraulically connected to one another over lines, and in each case the chamber and the subchamber are connected via adjustable valves arranged in the barrier wall, and for oscillation about an adjustable zero point, the hydraulic connection between two chambers lying on opposite sides of the working piston is closed and the valves between the chambers and the subchambers lying opposite the working piston are at least partially opened.

At least one sensor is allocated to the joint device and is coupled to a control device, and adjustment of the abutment is carried out on the basis of sensor values of the sensors which are allocated to the control device or coupled to the control device. The sensors are in particular position sensors, angle sensors or inclination sensors which are arranged on the upper part and/or the lower part and collect information regarding the angular positions or spatial positions of the upper part and/or the lower part. These detected sensor values are transmitted to the control device which evaluates them. The control device can for example be a microprocessor or a computer which is allocated to the joint device work or secured on the joint device or secured on a component arranged thereon. Via an adjustment device then either valves for hydraulic adjustment of the position of the abutment and/or working piston or other adjustment devices for the position of the respective abutment and/or piston are displaced, for example so as to set a zero position. On the basis of the parameters or characteristics detected during movement of the sensors, then even during the movement a corresponding displacement of the abutments and/or the working piston can ensue so as to compensate and adapt to specific movement patterns, environmental conditions, or conditions such as ramps or changes in the orthotic or prosthetic device or to react thereto.

BRIEF DESCRIPTION OF THE DRAWINGS

The invention is explained in more detail below with reference to the enclosed figures. The same reference signs designate the same components. Wherein:

FIGS. 14 to 19 show schematic sectional representations of the invention with three pistons in a cylinder subdivided by two barrier walls into three chambers hydraulically connected to one another;

DETAILED DESCRIPTION

Figure 1:
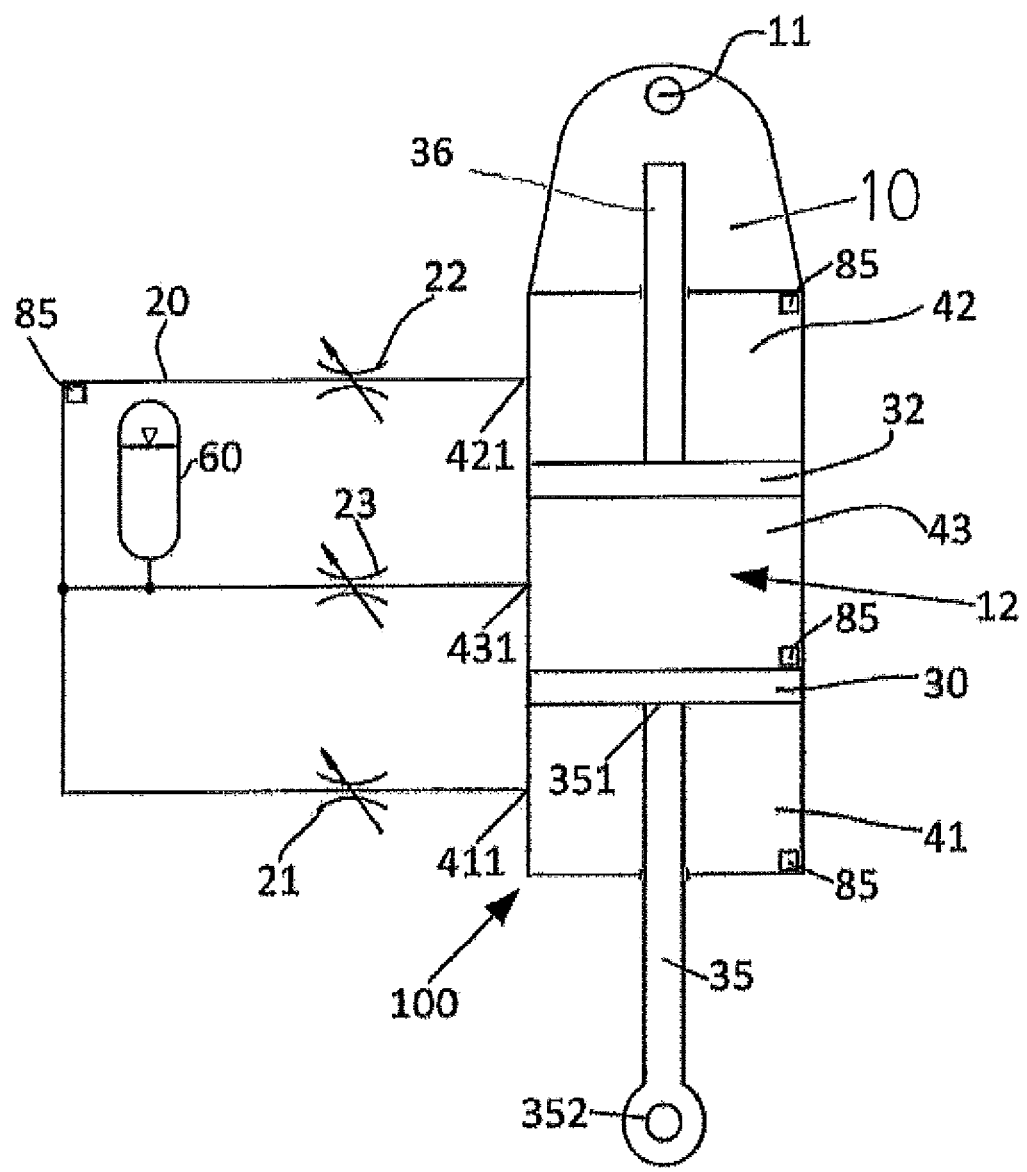
FIG. 1 shows a schematic representation of an actuator-damper-unit.

FIG. 1 shows an actuator-damper-unit 100 in a schematic representation for use in a prosthetic or orthotic device, for example in a prosthesis or orthesis. The actuator-damper-unit, hereinafter the AD unit, has a housing 10 in which a cylinder 12 is configured. In the exemplary embodiment shown, the cylinder 12 has a circular cross-section and receives a first piston 30, which is movably mounted along the cylinder wall. The shape of the piston can also be configured differently and can have a non-circular cross-section. On the first piston 30 a piston rod 35 is arranged, the first end 351 of which is connected to the first piston 30. The second end 352 opposite end 351 of the piston rod 35 can be secured to the prosthetic or orthotic device. The housing 10 has a fastening device 11 over which the housing 10 can be secured to a different prosthetic component or orthotic component. When the two orthotic or prosthetic components are displaced relative to one another, the piston 30 within the cylinder 12 is moved, so that a volume change of a first fluid chamber 41 occurs. Corresponding to a volume reduction of the first fluid chamber 41, the opposite volume of the cylinder 12, which is divided by the first piston 30, is increased. In this second volume, a second piston 32 is displaceably arranged along the longitudinal extension of the cylinder 30. The second piston 32 divides the second fluid chamber 42 so that between the two pistons 30, 32 a third volume-variable fluid chamber 43 is configured. Within each fluid chamber 41, 42, 43, a sensor 85 in the form of a pressure sensor can be arranged in order to be able to detect the predominant pressure in the specific fluid chamber 41, 42, 43. In another embodiment other sensors call be provided. The sensor data of the sensors 85 are transmitted to the control device which shall be explained in more detail below.

On the second piston 32 an additional rod 36 is arranged which extends out of the housing 10. If the second rod 36 has the same cross-section as the piston rod 35, in a pure displacement of both pistons 30, 32 without volume change of the middle fluid chamber 43, no compensating volume must be provided for the transported fluid. Such a compensating volume is necessary when only one piston rod 35 is present and the fluid, which preferably in the represented exemplary embodiment is configured as hydraulic fluid, is essentially incompressible. If one dispenses with the further rod 36, the volume displaced from the piston rod must be compensated, for example by means of a compensating volume.

Each of the fluid chambers 41, 42, 43 is provided with an access opening 411, 421, 431 through which the hydraulic fluid can flow in and out of the respective fluid chamber 41, 42, 43. The access openings 411, 421, 431 are connected to one another over the fluid lines 20. Upstream of each access opening 411, 421, 431 there is a switching or adjustment valve 21, 22, 23 arranged in the fluid line 20 in order to be able to set the flow cross-section of the fluid line 20 and thus also the hydraulic resistance.

Within the further volume-variable fluid chamber 43, a compressible medium or a spring can be arranged so that when the valves 22 are closed and the valve 23 is at least partially opened, the volume of the third fluid chamber 43 is reduced. In this way the compressible medium is compressed and energy is stored. Due to the volume change within the fluid chamber 43, it is necessary that a compensating volume 60 is allocated to the AD unit, so that a volume compensation, for example because of a leak, an entering piston rod, or temperature fluctuations, can take place. By means of an optional pressure sensor 85 the pressure in the compensation volume 60 can be measured, providing information regarding the reduction of the initial pressure due to fluid losses. If the valve 23 is closed, the third fluid chamber 43 behaves almost rigidly, so that normal damper hydraulics can be provided, for example with a flexion chamber 41 and an extension chamber 42. As soon as the valve 23 is opened again, the compressed medium or the spring, or the elastic element relaxes and the piston 30 is pressed outward counter to the compression direction, by which a corresponding movement in the orthotic or prosthetic device can be effected or supported.

Figure 2:
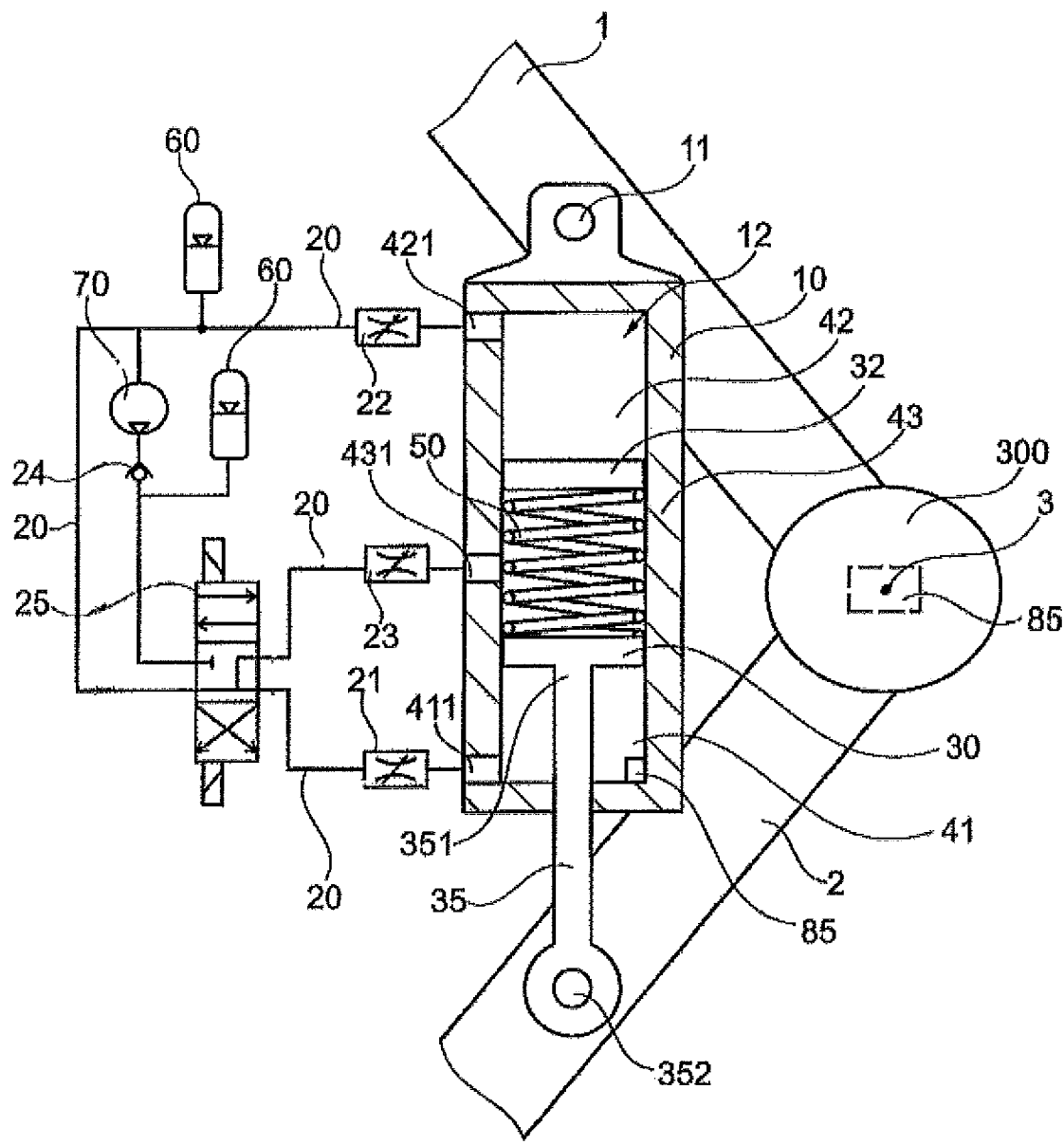
FIG. 2 shows a variant of FIG. 1 in the mounted state.

A variant of the invention is shown in FIG. 2, in which the AD unit with the housing 10 is secured to an upper part of an orthotic or prosthetic joint device via a fastening element 11, for example a bolt. On the upper part 1 a lower part 2 is rotatably mounted about a pivot axis 3, which is configured in a joint device 300. The joint device connects the upper part 1 to the lower part 2 and can be configured as a simple pivot axis 3 or as a polycentric element. The piston rod 35 of the piston 30 is pivotably secured on the second end 352 on the lower part 2. If the piston 30 is moved downward, the joint device is extended; if the piston 30 is moved upward, the joint angle is reduced and the joint device is flexed. Around the joint axis 3 a sensor 85 can be arranged so as to detect the relative position of an angle, for example, between the upper part 1 and the lower part 2, over which the positional data, for example angular data is transmitted to a control device 80. With a polycentric joint there is likewise sensor-based angular measurement but this can also be done over several sensors 85. The sensors 85 in the form of pressure sensors within the AD unit are only suggested and likewise supply control signals for the control unit 80, which is only suggested and controls a valve block, which can be part of the control unit 80. Alternatively or additionally, the position of the piston 30 and the force applied by the AD unit can be measured and transmitted to the control device 80.

The mechanical and hydraulic design of the exemplary embodiment according to FIG. 2 corresponds essentially to that of FIG. 1; here also there are three access openings 411, 421, 431 present, to each of which an adjustment valve 21, 22, 23 is allocated. The specific adjustment valve 21, 22, 23 is adjusted based on the control signals of the control unit 80 by means of the adjustment device, thus the flow cross-section of the fluid line 20 is enlarged, reduced, or blocked. In the exemplary embodiment shown, the compensation volume 60 may be acted upon with an initial pressure. Furthermore, so as to provide additional energy, a pump 70 is provided which is coupled by a check valve 24 in association with a compensation volume 60 or storage and a 3-way valve 25 to the hydraulic system of the AD unit. Additional potential or kinetic energy can be supplied via the pump 70 to the system so that when the energy stored within the further volume-variable fluid chamber 43 is not sufficient to initiate or implement the desired movement, additional movement energy can be provided. In addition the pump 70 can be used in addition to the stored mechanical energy. Likewise it is possible to supply the hydraulic system with energy via the pump 70 so that an energy storage 50, which is configured in the shown exemplary embodiment as a helical spring, can be loaded. The energy storage 50 is configured as an elastic element that can be configured both as a compressive element and as a tensile element. The embodiment of the energy storage as an elastic element is not limited to the specific embodiment.

In the shown switching position of the 3-way-valve 25, the pump 70 is decoupled. If the valve 25 is moved downward, a connection is established between the pump 70 and the third additional fluid chamber 43, so that here a pressure buildup can occur within the chamber 43 when the upstream adjustment valve 23 is opened. The other two fluid chambers 41, 42 are than connected to one another via the fluid line 20 and the valves 21, 22. If a volume increase occurs within the chamber 43 due to pressure applied to the pump 70, this is absorbed by the compensation volume 60.

If the 3-way-valve moves upward, the first fluid chamber 41 is acted upon via the pump 70 with hydraulic pressure, so that the volume of the third fluid chamber 43 is reduced, causing the spring 50 as energy storage to be compressed when the valve 23 is opened.

If the third valve 23 of the fluid chamber 43 formed between the pistons 30, 32 is blocked, and if the other two valves 23, 22 of the terminal fluid chambers 41, 42 are open, the AD unit is freely movable. The energy in the storage is dissipated when the valve 21 of the first valve chamber is blocked and the other two valves 22, 23 are opened. Energy is stored or released when the valve 22 of the upper fluid chamber 42 is closed and the other two valves 21, 23 are opened. If the upper valve 22 is opened and the valve 23 of the central fluid chamber 43 is throttled more strongly than the valve 21 of the first fluid chamber 41, energy is released, but in the direction of movement opposite to the storage movement.

Figure 3:
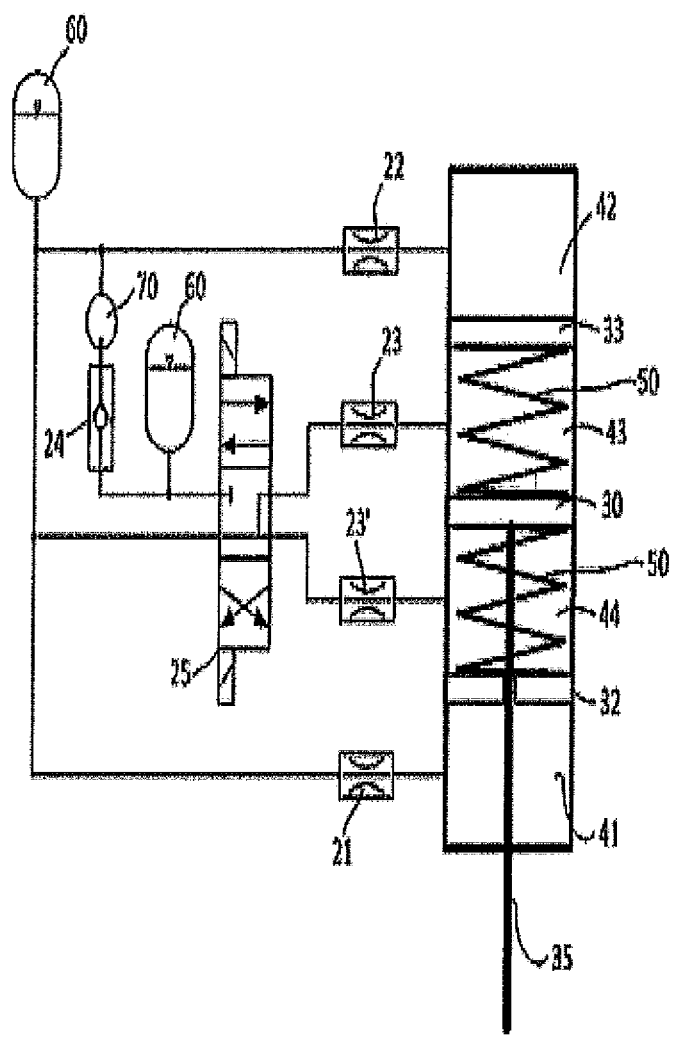
FIG. 3 shows a schematic representation of a variant with two additional pistons.

FIG. 3 shows a variant of the AD unit in which three pistons 30, 32, 33 are arranged in the housing so that altogether four fluid chambers 41, 42, 43, 44 are formed. In the exemplary embodiment shown, the piston 30, which is firmly connected to the piston rod 35, is arranged between the other two pistons 32, 33, wherein in the fluid chambers 43, 44 enclosed between the pistons 30, 32; 30, 33, in each case at least one energy storage 50 is arranged in the form of springs, pneumatic cushions, or elastomeric elements. Through the 3-way-valve 25, the two variable-volume chambers 43, 44 configured between the two pistons can be selectively filled with the hydraulic fluid from the pump. To this end the 3-way-valve 25 must be moved either to the right or left position. Likewise, pressure can be built up relatively easily in the two outer chambers 41, 42 in order to apply an active force in the flexion and extension direction. With such an embodiment of the AD unit, it is possible to optionally store and again release energy both in the flexion movement and in the extension movement. By additional switching of the pump 70 it is possible to provide a force intensification during the release of energy in the flexion and extension direction. Finally, an elastic oscillation of the middle piston 30 about the equilibrium position of the springs 43 and 44 can occur, so-called bouncing.

The AD unit can be used both as a pure damper as well as a pure actuator as well as a combination of damper and actuator. In the embodiment as a pure actuator, there must be no damping; in the embodiment as a pure damper, there must be no actuation or energy storage. Basically it is possible to configure the AD unit such that at least one of the three options for its use is implemented.

Figure 4:
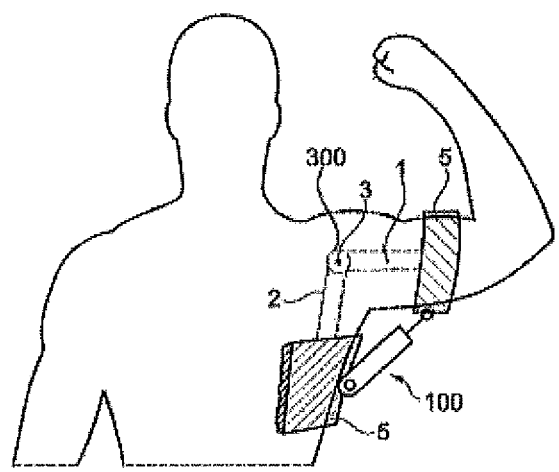
FIGS. 4 to 9 show exemplary applications of the actuator-damper unit.

FIG. 4 shows a first exemplary application of an actuator-damper unit 100 for supporting a shoulder joint. Here the actuator-damper unit 100 connects an optional upper part 1 via a fastening device 5 in the form of an upper arm cuff with an optional lower part 2 which likewise is secured via a fastening device 5 in the form of a thoracic shell 5 on the thorax of a patient. The lower part 2 is connected to the upper part 1 via a joint device 300 pivotably about a pivot axis 3. The upper part 1 and the lower part 2 are configured as the bar of an orthesis. Both fastening devices 5 are provided with receptacle devices for the piston rod 35 and the housing 10, so that upon entry or exit of the piston rod 35 into or out of the housing 10 the arm is spread out from the thorax or pulled toward it. Alternatively to coupling of the fastening devices 5 via a joint mechanism 300 with the pivot axis 3 in the upper part 1 and lower part 2, there is a possibility that the force return occurs directly over the body of the patient, thus over the skeletal structure, so that the upper part and the lower part are implemented by the fastening devices 5. The force transmission from the thoracic shell 5 to the floor occurs either through the body of the user or through an orthotic structure comprising the upper body and the lower extremity, similar to that of an exoskeleton.

Figure 5:
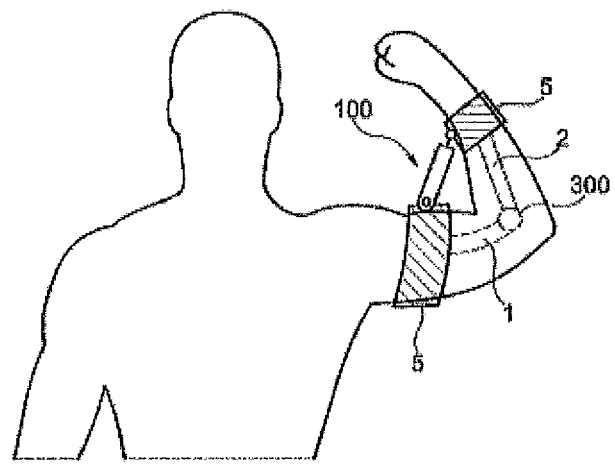

FIG. 5 shows a variant in the application in which the actuator-damper unit 100 is used for supporting the elbow joint. Here the actuator-damping device 100 uses a first fastening device 5 in the form of a forearm with a second fastening device 5 in the form of the upper arm shell or an upper arm cuff. Here also the orthotic or prosthetic device can consist solely of the actuator-damper device 100 and the two fastening devices 5 and optionally the force return can occur via an upper part 1 and a lower part 2 which are connected to one another via a joint device 300. The upper part 1 and the lower part 2 can each be configured as a bar. It is also possible to combine the embodiment according to FIG. 5 with the embodiment according to FIG. 4 so that along with a supported shoulder joint according to FIG. 4 a supported elbow joint can also be achieved. The further force delivery to the floor advantageously occurs via a further orthotic structure not shown or via an exoskeleton.

Figure 6:
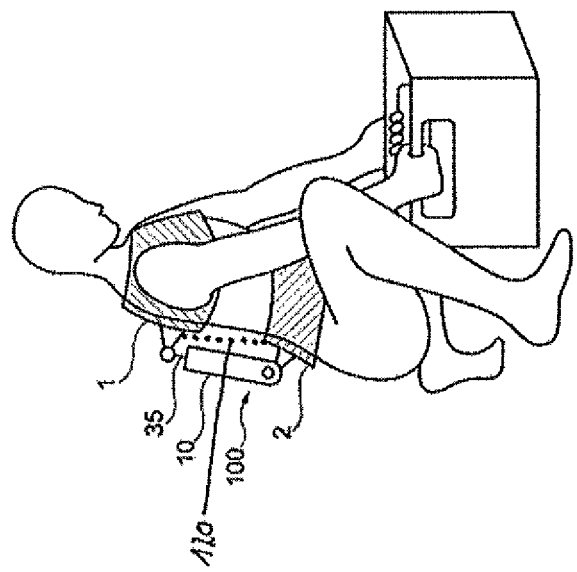

FIG. 6 shows a further variant in which the actuator-damper unit 100 is used for supporting the torso. The housing 10 is connected via a first bearing point with a lower part 2 in the form of a distal body shell in the region of the lumbar spine, in the exemplary embodiment shown, the piston rod 35 is connected to the upper part 1, but basically a reverse arrangement is also provided and possible so that the piston rod 35 can also be arranged on the lower part 2. Furthermore a cascade of several actuator-damper units 100 via several segments along the back or the spine is possible, and possibly the actuator-damper unit 100 can also be configured via to piston rods acting over several joints. A mechanical coupling 120 between the upper part 1 and the lower part 2 for implementation of an abutment for the actuator force is possible and is shown in the figure by a broken line.

Figure 7:
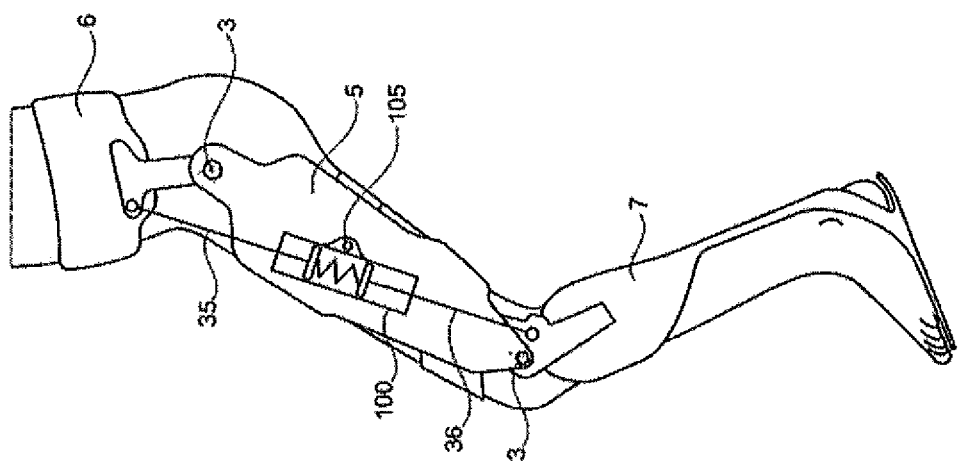

FIG. 7 shows an orthotic device in the form of an HKAFO (hip-knee-ankle-foot orthesis) in which the actuator-damper unit 100 is secured to an upper leg 5. The actuator-damper unit 100 has two separate pistons 30, 32 which are coupled to one another via a spring or an elastomeric element, and in each case are connected with a piston rod 35, 36. The piston rods 35, 36 engage once on a hip shell 6 and on a lower leg shell 7. The hip shell 6 is mounted pivotably via a joint about a joint axis 3 on the upper leg shell 5. The rotational axis 3 is at the height of the natural hip joint axis; a pivoting movement occurs from the entry or exit of the first piston rod 35 into or out of the housing 10. The second piston rod 36 is mounted on the lower leg bar 7 with an optional molded foot portion. The lower leg bar 7 is mounted via a joint pivotably about a pivot axis 3 relative to the upper leg shell 5. This pivot axis also lies at the height of the natural joint axis; the orthotic device engages several joints, in this case the knee joint, and the hip joint, wherein the actuator-damper unit 100 is rotatably mounted on the upper leg shell 5 via an attachment 105.

Depending on actuation of the actuator, the different entry and exit movements of the piston rods 35, 36 are effected, which results in pivoting of the respective components 5, 6, 7 with respect to one another. Likewise through the corresponding switching of the valves or activation of magnetic fields when magneto-rheological fluids are used, movement damping can be achieved. The principal of an orthesis or prosthesis with an actuator which engages over several joints may also be applied to other sections of the body, in particular for the knee and ankle joint, for segments of the torso or also for orthotic or prosthetic devices on an upper extremity.

Figure 8:
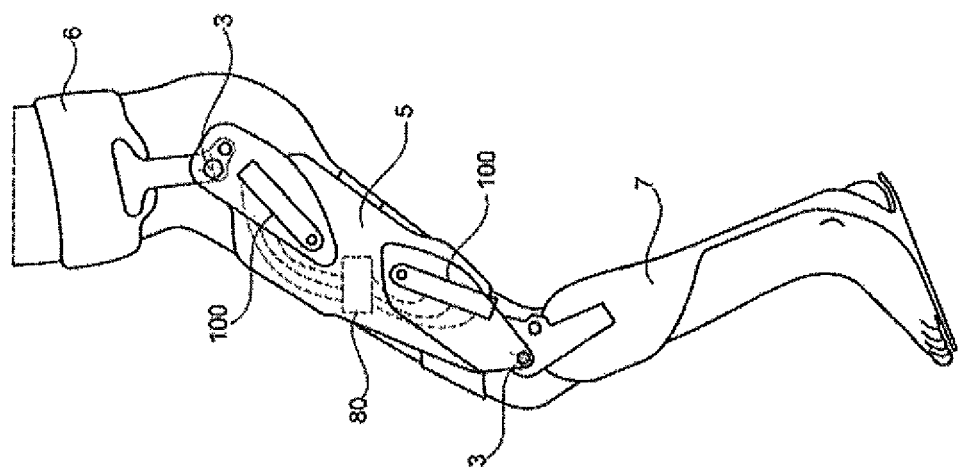

One variant of the embodiment of a joint engaging orthotic device is shown in FIG. 8, in which instead of an individual actuator or an individual actuator-damper unit 100, two actuator-damper units 100 are secured to an upper leg shell 5. The individual actuator-damper units 100 may be hydraulically coupled to one another, wherein in the hip engaging leg orthesis shown, a first actuator 100 is used for movement of the upper leg shell 5 relative to the hip shell 6 or cuff 6 in the region of the natural hip joint, while the second actuator 100 effects the knee movement by displacement of the lower leg bar 7 relative to the upper leg bar 5 about the rotary joint 3. Both actuators 100 can be hydraulically switched with one another via optional hydraulic lines which are shown by a broken line. For this purpose a control device 80 or a valve control block can be present in the lines, wherein by means of the valve control block KAD different switching variants allow an energy transfer between the respective actuators 100. Such a coupling is also possible between further actuators at other points, possibly on the knee or on the foot or between both legs. The control 80 can be computer supported and process sensor signals.

Figure 9:
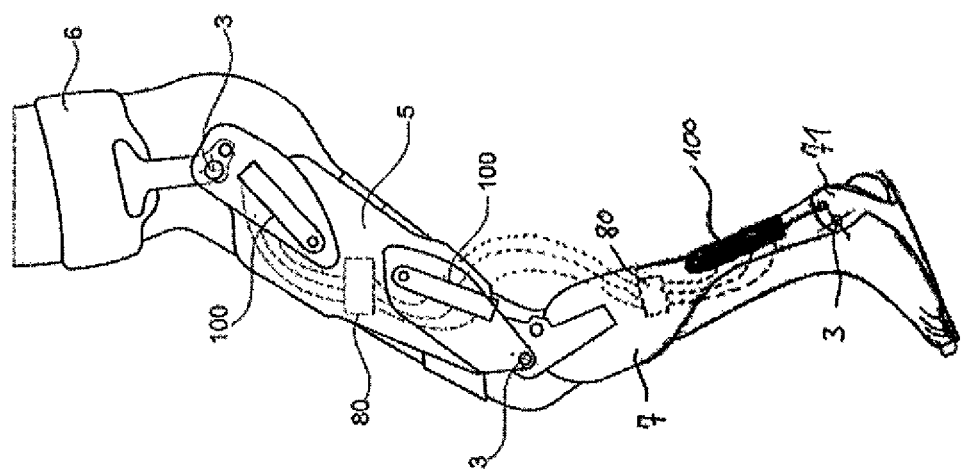

FIG. 9 shows a variant of FIG. 8 with a foot portion 71 which is movably mounted about a pivot axis 3 on the lower leg bar 7, which can be moved via an AD unit 100 in the direction of plantar flexion and dorsal flexion. The AD unit 100 mounted on the lower leg bar 7 is controlled via a separate control 80, possibly coupled to a control 80 mounted on the upper leg shell 5. The hydraulic streams can be coupled between the AD units 100 so as to allow a force transmission via the individual AD unit 100, so that fewer pumps or only one pump can be used. With the variant of FIG. 9 the foot portion is actuated or damped or blocked in its pivoting relative to the lower leg shell 7.

Figure 10:
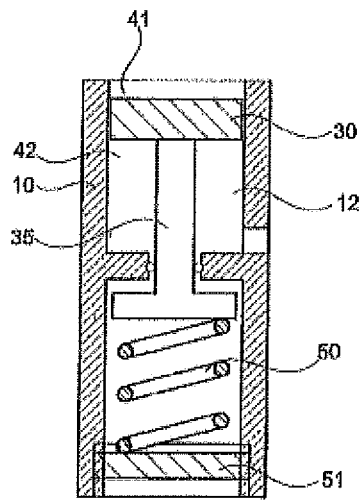
FIG. 10 shows a schematic representation of a piston with adjustable energy storage.

FIG. 10 shows an alternative form of the energy storage 50 in which the spring 50 of the spring storage lies outside of the fluid stream, in particular outside of a hydraulic fluid stream. To this end the piston rod 35 opposite the energy storage 50 in the form of the spring is sealed by a sealing ring so that the spring 50 does not come in contact with the hydraulic fluid, in particular hydraulic oil. This has the advantage that the energy storage 50 can also consist of a material that is incompatible with hydraulic fluid. Furthermore the energy storage 50 can be easily changed without having to open the oil circuit. To this end only an installation and retention disc 51 is removed from the housing 10, so that the spring 50 or the energy storage 50 can be easily removed. Using the disc 51 it is also possible to alter the pre-tensioning of the energy storage 50, for example when this disc 51 is screwed into the housing 10. A corresponding screw thread is suggested in FIG. 30. The oil pressure of the specific fluid chamber 42, 41 acts on the piston 30, which via the stamp at the end of the piston rod 35 compresses the energy storage 50 in the form of the spring. The oil from the second fluid chamber 42 comes from the low-pressure chamber via an opening in the low-pressure circuit, where a compensation volume is also located. The compensation volume receives the oil quantity dislocated by the piston rod 35. By using springs or energy storage 50 of varying stiffness, the storage characteristics can be influenced and adapted to the individual needs of different patients. A further adaptation to the individual desires of the patients can also be carried out via the adjustment screw or adjustment disc 51.

Figure 11:
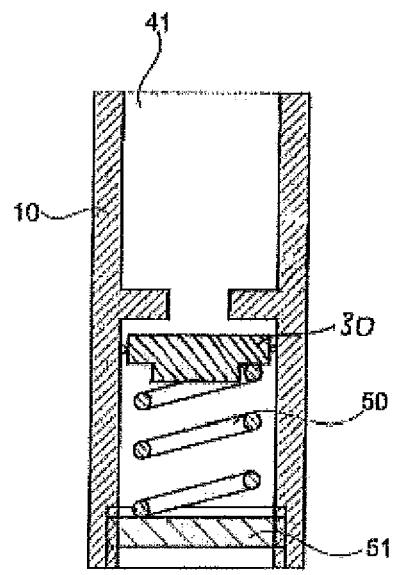
FIG. 11 shows a variant of FIG. 10.

One variant of FIG. 10 is shown in FIG. 11 in which the piston is mounted counter to a spring force by the energy storage 50 in the housing 10. Here the piston 30 is sealed opposite the housing inner wall so that the fluid from the chamber 41 compresses the spring 50 directly via the piston and no piston rod 35, no stamp, and no outlet channel are needed for the fluid displaced from the lower chamber 42.

Figure 12:
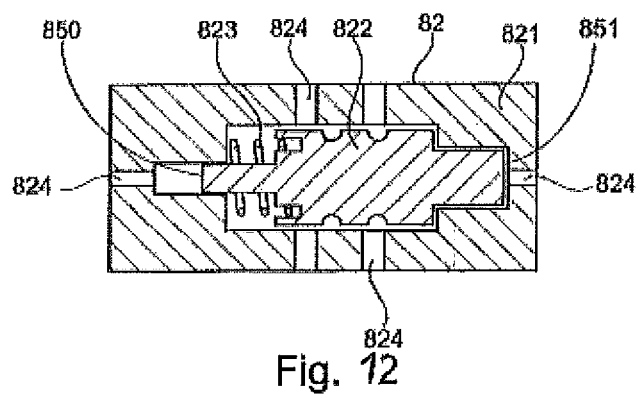
FIG. 12 shows a sectional representation of a mechanical pressure control valve.

FIG. 12 shows a schematic sectional representation of a mechanical pressure control valve 82 for a pressure storage with a valve body 821 and a switching element 822 which is movably mounted in the valve body 821 and is mounted via a spring 823 in a starting position. In the valve body 821 several connecting holes 824 are arranged for a pressure fluid, in particular a hydraulic fluid, that are connected with fluid lines. By different formation of the cross-sections 850, 851 a hysteresis can be implemented in the switch function, or the effect of the force of the return spring can be partially compensated.

Figure 13:
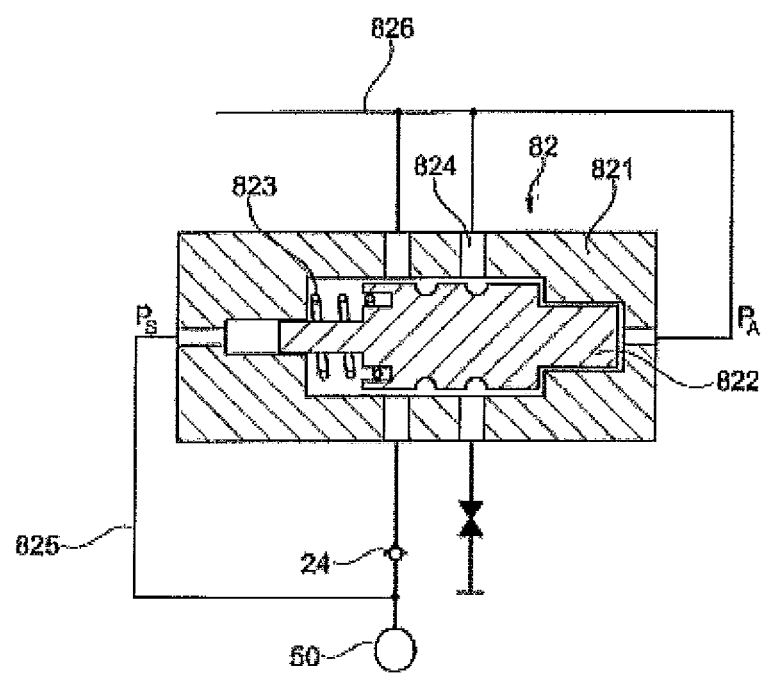
FIG. 13 shows an installation situation of a mechanical pressure control valve.

Hydraulic switching of the pressure control valve 82 is shown in FIG. 13. The moving switching element 822 is acted upon via a pressure line 825 with a fluid pressure $p_s$ from the pressure storage 50. The fluid pressure $p_s$ supports the pressure spring 823 and presses the switching element 822 into the starting position. If, via a working pressure line 826, hydraulic fluid is delivered from the actuator-damper unit, not shown, to the pressure control valve 82, the working pressure $P_A$ is applied to the switching element 822. The working pressure $P_A$ acts against the storage pressure $p_s$ and against the spring force of the spring 823. Within the movable switching element 822, circumferential grooves are arranged which in starting position make possible a passage from the working pressure side to a low-pressure side. If the working pressure $P_A$ is greater than the storage pressure p the switching element 822 is pushed to the left so that the left groove within the switching element 822 is aligned with the left holes within the valve body 862. In this way a flow connection is created from the working pressure side to the pressure storage 50, so that the working fluid does not reach the low-pressure side $P_L$, but loads the pressure storage 50. A return stream directly through the technical flow connection is prevented by the check valve 24. If the storage pressure $p_s$ is too great, the switching element 822 is again pushed to the right so that without diversion of a pressure for the pressure storage 50 the fluid can stream through the pressure control valve 82. Such a pressure control valve 82 does not require an electronic control action and can be operated without an external energy supply.

In FIGS. 14 to 19, a further variant of the invention is schematically represented. The actuator-damper unit 100 as a hydraulic unit has a housing 10 with a cylinder configured therein in which a first piston 30 as a working piston is displaceably mounted. The working piston 30 is coupled or at least be coupled via a piston rod 35, which projects from the housing 10, to a prosthetic or orthotic device, not shown; likewise the housing can be secured on another part of the orthotic or prosthetic device. Within the cylinder 12 there are two barrier walls 90 arranged which divide the cylinder 12 into a total of three chambers, namely into a middle main chamber and two outer secondary chambers. Within these chambers in each case there is a movably mounted piston 30, 32, 33 mounted. The working piston 30 connected to the piston rod 35 is arranged in the middle chamber and divides this main chamber into two fluid chambers 41, 42. In the secondary chambers separated by the barrier walls 90 the spring-loaded pistons 32, 33 are arranged as abutments which in the exemplary embodiment shown are arranged on the side of the specific barrier walls 90 facing the main chamber. The springs 50, which are supported both on the specific piston 32, 33 as well as the cylinder outer wall are arranged on the side facing away from the working piston 30 connected to the piston rod 35. The spring devices 50 are configured as compressive springs in the exemplary embodiment shown. By an opposite orientation of the spring devices 50, the working piston 30 can oscillate in both displacement directions, wherein the spring devices 50 can be released and tensioned in accordance with the direction of movement.

An adjustment valve 23, 23' and a check valve 24 are arranged within each of the barrier walls 90.

The spring pistons 32, 33 or abutment pistons subdivide the specific secondary chambers into fluid chambers 43, 44 which can be filled with hydraulic fluid, and a fluid-free chamber 43', 44'. Within the fluid-free chambers 43', 44', the energy storage or the spring device 50 is arranged, in the exemplary embodiment shown in the form of the spring or an elastomeric element. The piston rod 35 passes through a piston 33 so as to be able to extend out of the housing 10.

The fluid chambers 41, 42 divided by the working piston 30 via fluid lines 20, in which two adjustment valves 21, 22 and oppositely oriented check valves 24 are arranged, are hydraulically coupled to one another. Likewise the fluid-filled secondary chambers 43, 44 are connected to one another via a hydraulic line with oppositely oriented check valves 24. The connecting line of the secondary chambers 43, 44 is in addition coupled to the connecting lines between the first fluid chambers 41, 42 via a connecting line between the two check valves 24.

The exemplary embodiment thus represents a combination of three moving pistons 30, 32, 33 in three chambers and two energy storages 50 in the form of spring, devices. The energy storages 50 lie outside of fluid contact against the outsides of the spring pistons 32, 33, while a passive displacement of the working piston 30 via the change in movement resistors or drives lies on the inside. Alternatively, the spring devices 50 are arranged outside of the housing 10 and are coupled via piston rods, for example, or hydraulic lines or pneumatic lines to the specific abutment 32, 33. The passages through the barrier walls 90 via the adjustment valves 23, 23' or the check valves 24 can be arranged in the barrier walls 90 themselves or can be configured via channels running on the outside on the housing 10 with the corresponding valves. Via the control valves 23, 23'2 and the check valves 24, the spring pistons 32, 33 are blocked from the circuit, or damping is effected. Likewise the passive displacement of the working piston 30 can be blocked by means of the two-way switch of the hydraulic line running parallel to the working piston 30 and arranged outside of the housing 10.

For the case that a hydraulic compensation is blocked by the outside adjustment valves 21, 22 and only the passages to the spring pistons 32, 33 as abutments for the spring devices 50 via the valves 23, 23' are opened, a volumetric compensation of the hydraulic fluid takes place via the springs. The volume of fluid-filled secondary chambers 43, 44 will vary in this case depending on the position of the working piston 30. For the case when an active displacement is blocked and only a passive displacement should take place via the outside valves 21, 22, 24, a volumetric compensation must be considered; here in each case the corresponding adjustment valve 21, 22 must be opened.

Figure 14:
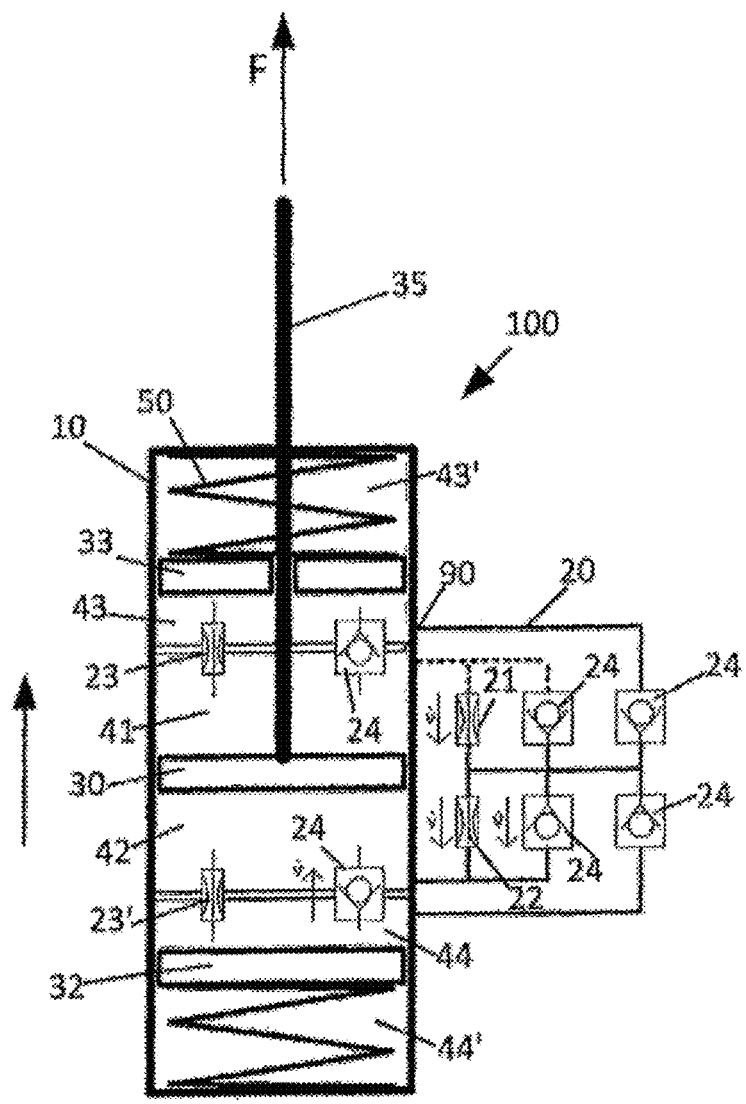

In FIG. 14, when there is an outward movement of the piston rod 35, for example during an extension, the working piston 30 is moved in the direction of the arrow. In this way the pressure in the upper fluid chamber 41 is increased and high-pressure fluid flows against the first check valve 24 and through the first adjustment valve 21, as indicated by the arrow, through the second adjustment valve 22 into the lower fluid chamber 42. Likewise the lower energy storage 50 releases energy by relaxing, causing the hydraulic fluid to be conveyed through the lower check valve 24 to the lower fluid chamber 42. The adjustment valves 23, 23' are closed, so that a movement damped via the valves 21, 22 in the extension direction is produced.

Figure 15:
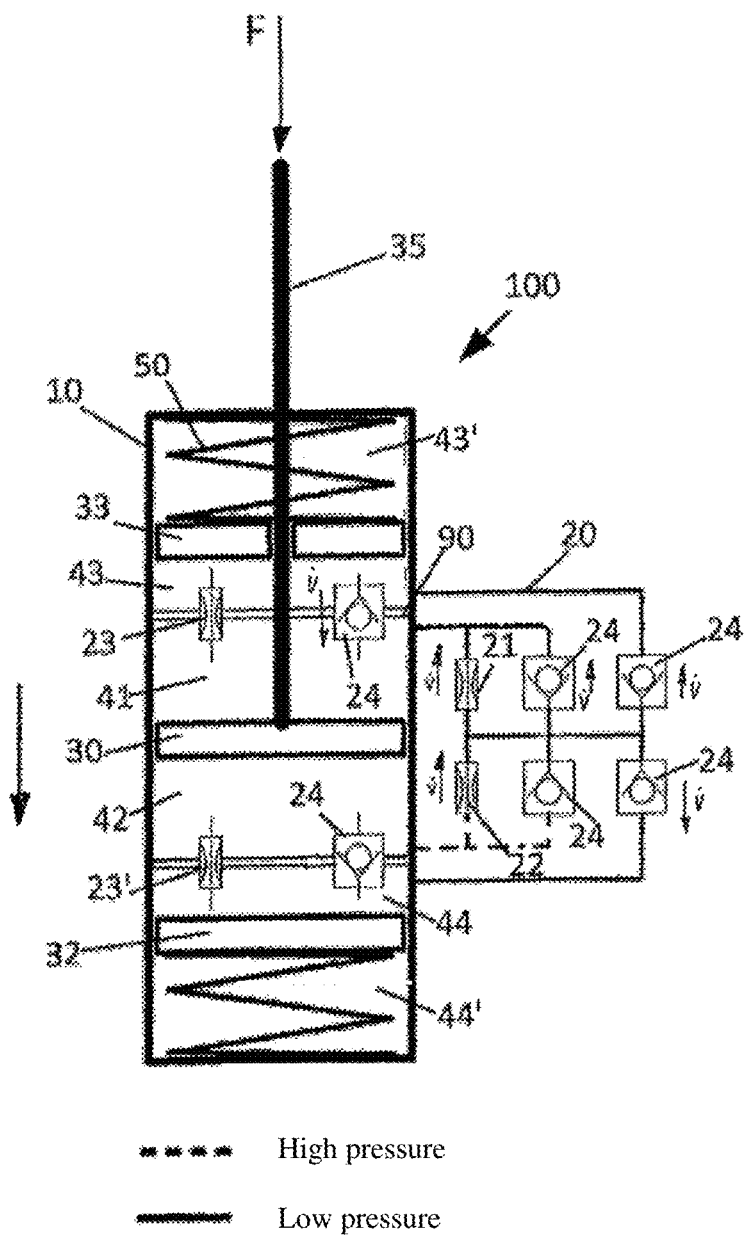

In a movement reversal, which is shown in FIG. 15, the adjustment valves 23, 23' in the barrier walls 90 continue to be closed, while the adjustment valves 23, 23' in the outside hydraulic switch are opened. When there is an incoming movement of the piston rod 35, for example when there is flexion, the hydraulic fluid flows from the lower fluid chamber 42 through the high-pressure line and the lower adjustment valve 23', the upper adjustment valve 23, and the two check valves 24 both to the upper fluid chamber 41 of the working piston 30 and to the upper fluid chamber 43 of the spring piston 31. Due to the pressure within the connecting line between the check valves 24, which connects the fluid chambers 43, 44 of the spring pistons 32, 33 to one another, at the same time a fluid stream is directed into the fluid chamber 44 of the lower spring piston 32. The upper energy storage 50 is relaxed, since it is arranged on the low-pressure side, so that hydraulic fluid can flow out of the upper fluid chamber 43 through the check valve 24 to the upper fluid chamber 41 of the working piston 30.

Figure 16:
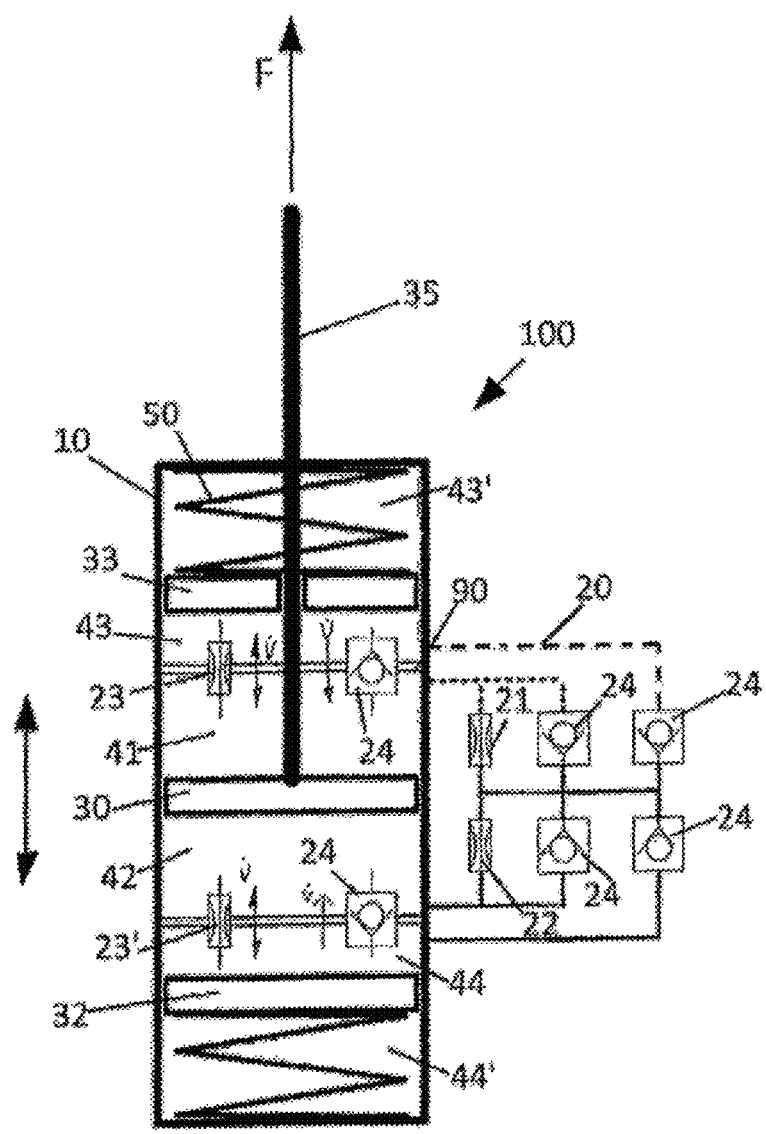

In FIG. 16 the valves 23, 23' are opened, while the external adjustment valves 23, 23' are closed. Due to the opened valves 23, 23', a back-and-forth movement of the piston 30 is possible, as suggested by the double arrow, since the springs 50 in the secondary chambers can be relaxed or compressed. The outer flow path is blocked, so that a volume exchange is possible only between the fluid chambers 41, 43, and 42, 44 in each adjacent to one another through the valves 23, 23' and the check valves 24.

Figure 17:
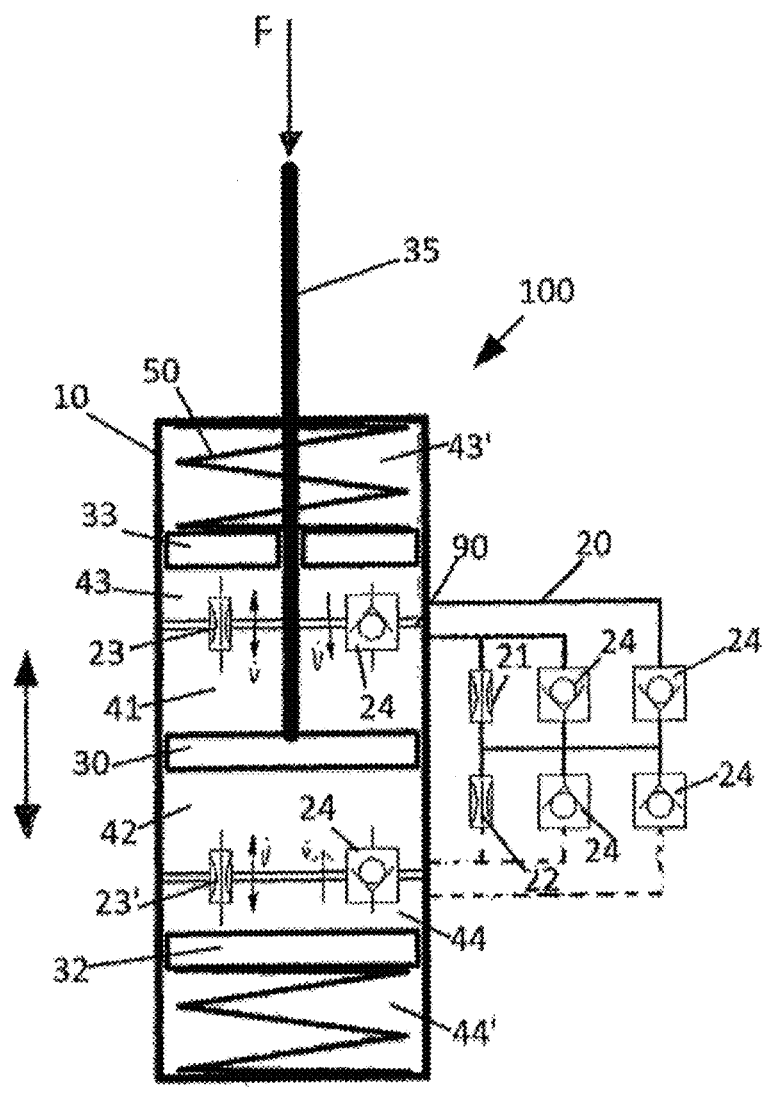

FIG. 17 represents the situation in which the valves are switched analogously to FIG. 16, but a pressure force is exercised on the piston rod 35 and the working piston 30 is pressed downward. Accordingly the high-pressure side is on the lower side of the working piston 30 and when a force is applied downward, as shown by the arrow on the piston rod 35, leads to compression of the lower spring 50 upon entry of the piston rod 35, for example during flexion, and to unloading of the upper energy storage 50. The energy storages 50 behave accordingly when there is a reverse movement, thus when there is an outward movement of the piston rod, or when there is an extension movement as shown in FIG. 16.

Figure 18:
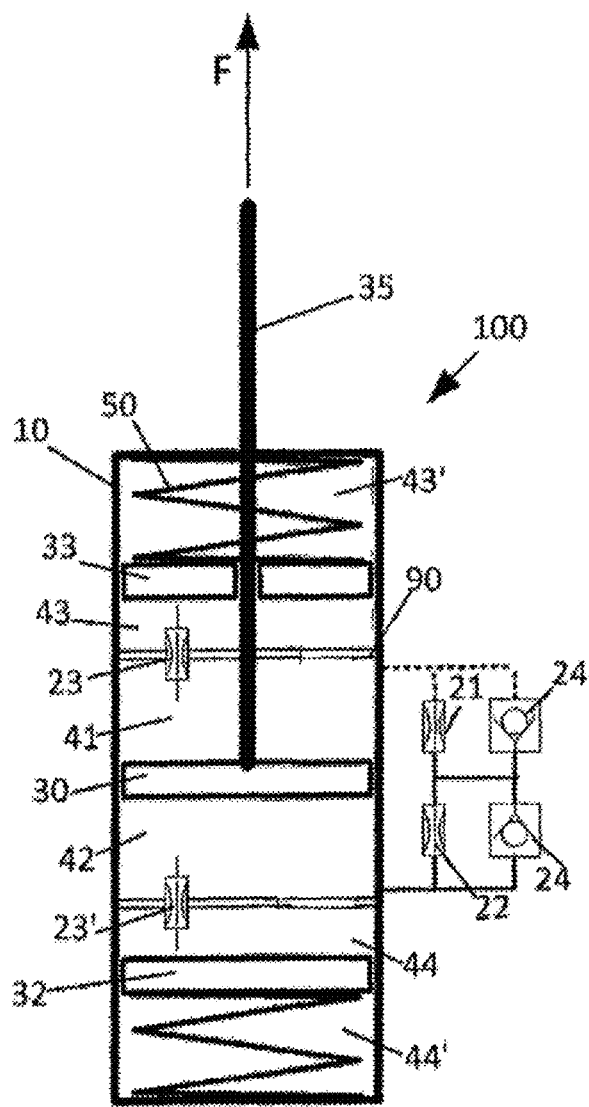
Figure 17:
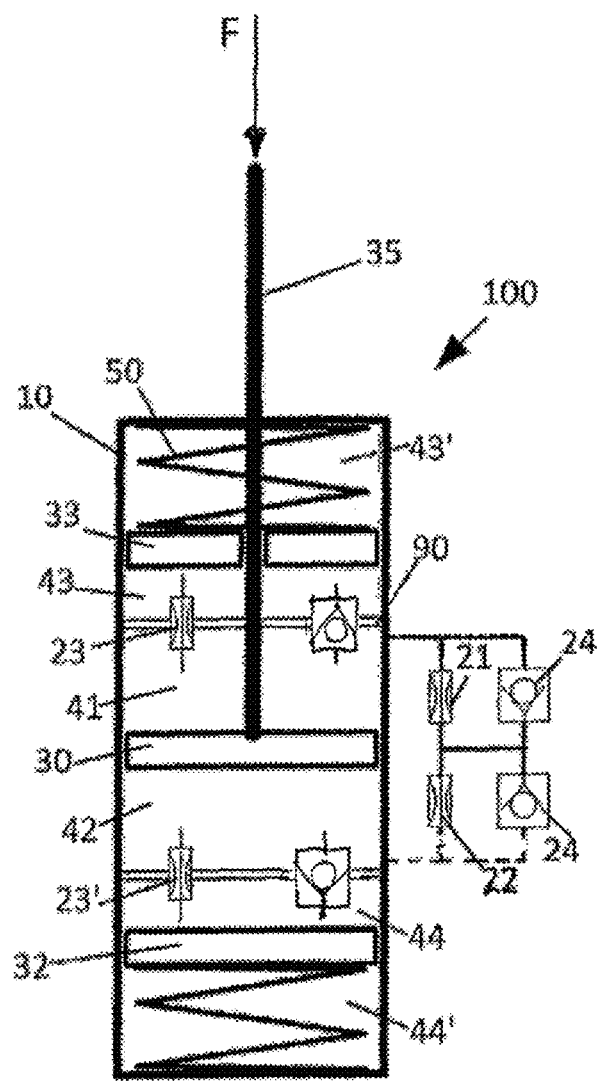

FIG. 18 shows the situation in which all valves 21, 22, 23, 23' are closed. Even upon application of a tensile force OR the piston rod 35, movement of the working piston 30 is blocked; the same applies to the reverse force application, which is shown in FIG. 19.

All embodiment of the hydraulic unit 100, as it was described in detail in FIGS. 14 to 19, can also be used in the hydraulic units, which are designated as actuator-damper units 100 and were described with reference to other figures.

Figure 20:
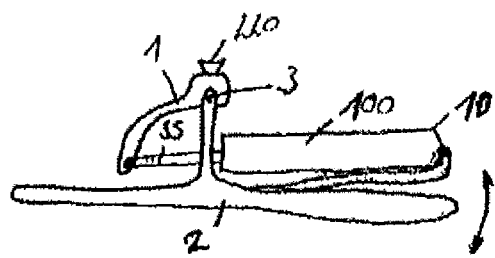
FIG. 20 shows an exemplary application of the hydraulic unit in a prosthetic foot.

FIG. 20 shows an exemplary application of the hydraulic unit 100 on a prosthetic foot with a lower part 2 in the form of a bottom part of a prosthetic foot, on which an upper part is displaceably arranged about a pivot axis 3 with a pyramid adapter 220 for fastening to a lower leg tube. The upper part 1 is connected to a piston rod 35 of the hydraulic unit 100, which is mounted on the opposite end of the piston rod 35 to the housing 10 on a bracket of the lower part 2. By means of a change in the abutments as described above, and the associated displacement of the zero position, it is possible to displace a starting position of the upper part 1 relative to the lower part 2, and thus to adapt the prosthesis foot to different heel heights. The pivoting and adaptation to the zero position are shown by the double arrow.

Figure 21:
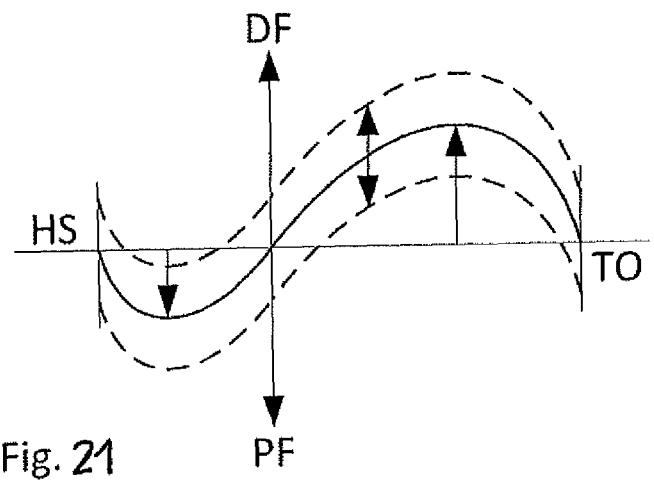
FIG. 21 shows the angular path of a prosthesis foot.

FIG. 21 shows the approximate angular path between the upper part 1 and the lower part 2 during application in a prosthetic foot or an orthotic food, for example as sketched in FIG. 40. After placement, the so-called heel strike HS, plantar flexion PF occurs, thus a displacement of the sole in the direction of the floor. Alter the sole lies complete on the floor, the upper part 1 is displaced forward about the pivot axis 3 in the direction of walking, the plantar flexion angle again diminishes until the lower leg tube is in a vertical position. Then in the course of a further forward pivot of the lower leg tube in the walking direction, a dorsal flexion proceeding from the zero position is initiated. The zero position is achieved during a passage of the curve of the plantar flexion PF to the dorsal flexion DF. In the further course of a step, there is a so-called roll-over and a diminishing dorsal flexion angle, until the standing phase during walking is concluded, when the prosthetic foot leaves the floor in a toe-off TO. The two broken lines shown above and below the solid line show the possibilities of displacement of the zero position. If the upper line is adjusted, the zero position is displaced in the direction of dorsal flexion; if the lower line is adjusted, the zero position is displaced in the direction of plantar flexion.

Figure 22:
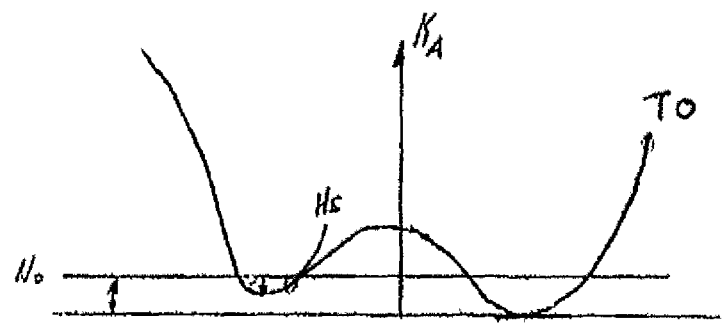
FIG. 22 shows a knee angular path during walking.

FIG. 22 shows an example of a knee angle course $K_A$ with a zero crossover $N_0$ which as suggested by the double arrow, can be displaced. Coming from the swing phase, the lower leg passes through an increasing knee angle and compresses the spring device downward after stepping over the line $N_0$. An extension movement occurs against the pretensioning by the spring due to mass inertia. After the heel strike HS, flexion of the knee joint by relaxation of the pretensioned spring device is supported to the point of maximal standing phase flexion after which, during the rollover, a standing phase extension occurs, again against the spring force of the spring device when the him $N_0$ is exceeded. The energy stored in the spring device when the zero position $N_0$ is exceeded can then be released again at the end of the standing phase, and serves to support the flexion movement and initiate the swing phase after the heel strike or the toe-off TO.

The invention claimed is:

1. A joint device comprising:
    an upper part and a lower part which are mounted on each other so as to be pivotable about a pivot axis;
    a hydraulic unit secured on the upper part and the lower part;
    a housing;
    a cylinder arranged in the housing;
    a working piston arranged in the cylinder, connected to a piston rod, mounted displaceably, and arranged to divide the cylinder into two chambers;
    at least one spring device coupled to the working piston and configured to transmit tensile forces and compressive forces and engage on at least one abutment which is arranged inside the cylinder.

2. The joint device according to claim 1, wherein the abutment is mounted as a displaceably mounted separating element or piston in the chamber and separates at least one subchamber from the chamber.

3. The joint device according to claim 2, wherein the chambers and at least one subchamber are hydraulically connected to one another via channels in which adjustable valves are arranged.

4. The joint device according to claim 2, wherein the chambers are hydraulically coupled to one another via channels in which adjustment valves are arranged.

5. The joint device according to claim 1, wherein the abutment limits the chambers on the outside and a non-displaceable barrier wall separates at least one subchamber from the chambers.

6. The joint device according to claim 5, wherein in each case the chambers and the at least one subchamber are connected to one another via the adjustable valves arranged in the barrier wall.

7. The joint device according to claim 1, wherein the spring device is arranged within one of the chambers.

8. The joint device according to claim 2, wherein the at least one spring device comprises at least two spring devices, wherein the at least one subchamber comprises at least two subchambers, and wherein the at least two spring devices are each arranged in a different subchamber of the at least two subchambers.

9. The joint device according to claim 1, wherein the spring device holds the upper part in an adjustable starting position relative to the lower part.

10. The joint device according claim 1, wherein the joint device is arranged in a prosthetic or orthotic foot or a prosthetic or orthotic knee joint.

11. The joint device according to claim 1, wherein two abutments are present in the hydraulic device, and are arranged on opposite sides of the working piston from one another.

12. A method for setting and operating a joint device, the method comprising:
providing the joint device having an upper part and a lower part, which are mounted on each other so as to be pivotable about a pivot axis, with a hydraulic unit secured on the upper part and the lower part, with a housing in which a cylinder is arranged, in which a working piston connected to a piston rod is mounted displaceably and divides the cylinder into two chambers, wherein the working piston is coupled to at least a spring device which transmits tensile and compressive forces and which engages on at least one abutment mounted displaceably in a chamber of the chambers;
opening or adjusting valves in channels to set a zero position of the working piston or control a pivoting movement of the upper part relative to a lower part.

13. The method according to claim 12, wherein each abutment separates a subchamber from the respective chamber of the chambers, and the chambers and the respective subchambers are hydraulically coupled to one another via the lines and valves and the valves are closed to block the joint device.

14. The method according to claim 13, wherein the abutment limits the chambers on the outside and a non-displaceable barrier wall separates the at least one subchamber from the chambers, and the chambers are hydraulically coupled to one another via the lines and the chambers and the corresponding subchambers are connected by adjustment valves and the valves are closed to block the joint device.

15. The method according to claim 13, wherein oscillation of the joint device about an adjustable zero point opens the hydraulic connection between two subchambers lying on opposite sides of the working piston and closes the connection between the chambers.

16. The method according to claim 12, wherein the abutment separates each of the chambers into two subchambers, and the chambers and the subchambers are hydraulically coupled to one another via lines and valves, and the valves allocated to the chambers are opened to release the joint device.

17. The method according to claim 13, wherein the abutment limits the respective chamber of the chambers on the outside and a non-displaceable barrier wall separates the at least one subchamber from the respective chamber of the chambers, and the chambers are hydraulically coupled to one another via lines and each chamber and a corresponding one of the subchambers are connected via adjustment valves arranged in the barrier wall, and the valves are opened to release the joint device.

18. The method according to claim 12, wherein the valves are only partially opened for damping the pivoting movement.

19. The method according to claim 12, wherein the abutment limits the chambers on the outside, each abutment separates a sub-chamber from the respective chamber of the chambers and a non-displaceable barrier wall separates the at least one subchamber from the chambers, and the chambers are hydraulically coupled to one another via lines and each chamber and the corresponding subchamber are connected via the adjustment valves arranged in the barrier wall, wherein oscillation about an adjustable zero point, closes the hydraulic connection between the two chambers lying on opposite sides of the working piston, and at least partially opens the valves between the chambers opposite the working piston and the at least one sub-chamber.

20. The method according to claim 12, wherein at least one sensor is allocated to the joint device and is coupled to a control device, and adjustment of the abutment takes place on the basis of sensor values.

* * * * *